United States Patent [19]

Afanasiev et al.

[11] Patent Number: 4,656,259

[45] Date of Patent: Apr. 7, 1987

[54] METHOD FOR PREPARING N-ALKYL-N'-GLYCOSYL-N-NITROSOUREA

[75] Inventors: Vitaly A. Afanasiev; Zhenis A. Dzhamanbaev, both of Frunze, U.S.S.R.

[73] Assignee: Institut Organicheskoy Khimii Akademii Nauk Kirgizskoi, Frunze, U.S.S.R.

[21] Appl. No.: 769,760

[22] Filed: Aug. 26, 1985

Related U.S. Application Data

[63] Continuation of Ser. No. 509,031, Jun. 29, 1983, abandoned.

[51] Int. Cl.$^4$ .............................................. C07H 1/00
[52] U.S. Cl. ..................................... 536/22; 536/55.3; 536/124
[58] Field of Search ....................... 536/22, 55.3, 124; 564/33

[56] References Cited

U.S. PATENT DOCUMENTS

| | | | |
|---|---|---|---|
| 4,086,415 | 4/1978 | Suami et al. | 536/17.2 |
| 4,182,757 | 1/1980 | Tsujihara et al. | 424/180 |
| 4,220,643 | 9/1980 | Suami | 424/180 |

OTHER PUBLICATIONS

Afanasiev et al., Urea N–Glycoside, Chem Abstracts 79: 78153c (1973).
Dzhamanbaev et al., Synthesis and Properties of N–Glycosylureas, Chem Abstracts 97: 92673a (1982).
Battelle Memorial Institute, Feed for Ruminants, Chem Abstracts 90: 202494h (1978).

Primary Examiner—Johnnie R. Brown
Attorney, Agent, or Firm—Burgess, Ryan & Wayne

[57] ABSTRACT

A method for preparing an N-alkyl-N'-glycosyl-N-nitrosourea which comprises reacting a non-protected monosaccharide with an alkylurea in the presence of nitroaniline in an organic medium, followed by nitrosation of the reaction product.

7 Claims, No Drawings

METHOD FOR PREPARING N-ALKYL-N'-GLYCOSYL-N-NITROSOUREA

This application is a continuation of application Ser. No. 509,031, filed June 29, 1983, now abandoned.

FIELD OF THE INVENTION

The present invention relates to the chemistry of carbohydrates and, more specifically, to glycosylurea derivatives; more particularly, it relates to the preparation of N-alkyl-N'-glycosyl-N-nitrosourea.

N-alkyl-N'-glycosyl-N-nitrosourea is a promising biologically active substance which is useful in medicine as an active ingredient for the preparation of antitumor compositions.

BACKGROUND OF THE INVENTION

It is known that glycosylurea derivatives manifest biologically active properties and are useful in medicine as active components for the preparation of pharmaceutical compositions. It is also known that glycosylurea derivatives subjected to nitrosation result in substances possessing antitumor properties.

Methods for the synthesis of glycosylnitrosourea with different positions of N-nitrosourea fragments in the carbohydrate ring and with different substituents have been developed in the attempts to obtain selective-effect preparations possessing a good water-solubility and a low toxicity.

The synthesis of these derivatives is based on a general procedure involving interaction of glycosylamine with alkylisocyanates and nitrosation of the reaction products with such nitrosation agents as $NaNO_2$, $NOCl$, $N_2O_3$, $C_5H_{11}NO$ (cf. U.S. Pat. No. 4,157,439; U.S. Pat. No. 4,156,777; British Patent Application No. 1,539,500; No. 1,507,099; J. Med. Chem., 1979, 22, No. 3, 314–316; J. Med. Chem., 1975, 18, 104).

Numerous glycosylnitrosourea derivatives have been prepared by the reaction of a monosaccharide with an alkylamine, followed by treatment of the resulting glycosylamines with an alkylisocyanate. The reaction results in the preparation of substituted anomeric glycosylurea derivatives which, under the effect of formic acid, are isomerized into a thermodynamically stable form of glycosylurea. The thus-obtained glycosylurea is subjected to nitrosation to give glycosylnitrosourea derivatives (J. Med. Chem., 1982, 25, No. 4, 441–446; Chem. Pharm., Bull 1982, 30, 534–543).

Known in the art is a method for the synthesis of N-chloroethyl-N'-(β-D-glycosyl)-N-nitrosourea comprising reacting poly-O-acetyl-glycosylamines with chloroethylisocyanate in an inert medium, followed by desacetylation of the resulting poly-O-acetyl-glycosyl-chloroethylurea. Then the desacetylation product is subjected to nitrosation (cf. Bull. Chem. Soc., Japan 48 (12), 3763 (1975)).

Also known is a method for preparing N-alkyl-N'-(β-D-glycosyl)-N-nitrosourea from polyacetyl-glycopyranose. Polyacetylglycopyranose is synthesized according to a known procedure (P. A. Levene et al., J. Biol. Chem., 90, 89 (1931). Polyacetylglycopyranose is treated with HBr, the resulting poly-O-acetylglycosyl-bromide is reacted with $NaNO_3$ and the thus-obtained poly-O-acetylglycosylazide is hydrogenated in the presence of Raney nickel or platinum, or palladium under the pressure of 3.4 kg/cm². As a result, poly-O-acetyl-glycosylamine is obtained which is reacted with an alkylisocyanate, followed by isolation of poly-O-acetyl-(β-D-glycosyl)alkylurea. The poly-O-acetyl-(β-D-glycosyl)-alkylurea is desacetylated and then subjected to nitrosation, followed by isolation of the desired product (cf. U.S. Pat. No. 4,086,415). However, this method consists in many steps and is difficult to perform on a commercial scale.

OBJECT OF THE INVENTION

It is an object of the present invention to simplify and render less expensive the process for preparing an N-alkyl-N'-glycosyl-N-nitrosourea.

SUMMARY OF THE INVENTION

The object of the present invention is accomplished by a method for preparing an N-alkyl-N'-glycosyl-nitrosourea of the formula:

(I)

wherein R is glycosyl, R' is a lower alkyl; according to the present invention this method is characterized in that a non-protected monosaccharide is reacted with an alkylurea of the formula:

(II)

wherein R' is a lower alkyl, in the presence of nitroaniline and a mineral acid in an organic medium, followed by nitrosation of the resulting reaction product. It is advisable that the process be conducted at the boiling temperature of the mixture. The amount of nitroaniline for the reaction ranges from 1.6 to 3.5% by mass.

DETAILED DESCRIPTION OF THE INVENTION

As it has been mentioned hereinbefore, the desired product, namely; an N-alkyl-N'-glycosyl-N-nitrosourea of the above formula (I) is prepared by reacting a non-protected monosaccharide with an alkylurea of the above formula (II). The starting components, i.e. the monosaccharide and the alkylurea, can be used in the molar ratio of 1:1 or 1:1.2. The reaction is carried out in the presence of nitroaniline and a mineral acid in an organic medium. The content of nitroaniline for the reaction ranges from 1.6 to 3.5% by mass. This amount is enough for carrying out the process within a short period. If the amount of nitroaniline is less than 1.6% by mass, the reaction would proceed but slowly and its duration would be extended which is undesirable. Increasing the amount of nitroaniline above 3.5% by mass would not give any additional advantage in reduction of the process duration, but can result in overconsumption of the reagent. It is desirable to carry out this reaction at the boiling temperature of the mixture. In this case the process proceeds more intensively. As a result of the reaction, an intermediate product is obtained as a precipitate which is then separated. Then the intermediate is subjected to nitrosation by sodium nitrite in the presence of glacial acetic acid at a temperature of from 0° to −2° C. The product yield ranges from 62 to 90%.

As the starting monosaccharides use can be made of D-xylose, D-arabinose, D-mannose, G-glucose, D-galactose, L-arabinose and other similar monosaccharides. As the alkyl-urea use may be made of methyl-, ethyl-, propyl and butyl-urea. The process for the preparation of N-alkyl-N'-glycosyl-N-nitrosourea is conducted under normal pressure.

The method according to the present invention has a number of advantages over the prior art process disclosed in U.S. Pat. No. 4,086,415. The process of this invention is rather simple, it is two-staged, necessitates no expensive and hardly-available components, nor high power consumption; it neither takes long time to perform.

The use of nitroaniline in the reaction of glycosylation of an alkylurea makes it possible to reduce the process duration by 6 times as compared to the above-mentioned prior art process consisting in 6 stages. One of the most important advantages of the method according to the present invention resides in that, according to the invention, as the starting monosaccharide use is made of a non-protected monosaccharide which enables a considerable simplification of the process for preparing the desired product. The use of a non-protected monosaccharide makes it possible to avoid such operations as protection of hydroxy groups of a monosaccharide and further operations associated with elimination of these groups. The use of a non-protected monosaccharide does not affect the yield of the desired product and its quality. Therefore, the use of a non-protected monosaccharide makes it possible to considerably simplify the process and make it less expensive, while retaining good quality and yield of the product.

Another advantage of the method according to the present invention resides in that the process is conducted under normal pressure, wherefore no special equipment is required.

Another important advantage of the method according to the present invention is that it can be readily implemented on a commercial scale.

Taking into consideration the simplicity and inexpensiveness of the process according to the present invention, as well as a high yield of the product, it is quite clear that this process can be commercially advantageous over the prior art processes.

For a better understanding of the present invention some specific examples illustrating the process are given hereinbelow.

EXAMPLE 1

Preparation of
N-methyl-N'-($\beta$-D-glucosyl)-N-nitrosourea

A mixture of 3.6 g of D-glycose, 1.8 g of methylurea, 0.2 g of nitroaniline and 0.13 ml of a concentrated hydrochloric acid in 20 ml of methanol is heated at reflux for 20 minutes. The formed precipitate in the amount of 2.85 g is separated and added with 10 ml of glacial acetic acid, 3 ml of distilled water, 1.65 g of sodium nitrite and stirred for 2 hours at the temperature of $-2°$ C. The solution is evaporated, the residue is recrystallized from ethanol. The product yield is 2.88 g (90% of the theoretical). M.p. 180° C. with decomposition, $[\alpha]_D - 19°$ (water), $R_f = 0.56$. Found, % N 15.62. Calculated, %: N 15.84.

In this Example and hereinafter the $R_f$ is determined in the system: benzene-butanol-pyridine-water 1:5:3:3.

EXAMPLE 2

Preparation of
N-methyl-N'-($\beta$-D-galactosyl)-N-nitrosourea

A mixture of 3.6 g of D-galactose, 1.8 g of methylurea, 0.2 g of nitroaniline and 0.3 ml of a concentrated hydrochloric acid in 20 ml of methanol is refluxed for 25 minutes. The resulting precipitate in the amount of 3.2 g is separated and added with 15 ml of glacial acetic acid, 3 ml of distilled water, 1.86 g of sodium nitrite and stirred for 2 hours at the temperature of $-1°$ C. The residue is filtered off, washed with an alcohol to give 2.51 g of the product (70% of the theoretical). M.p. 121° C., $[\alpha]_D + 21.8°$ (water). $R_f = 0.53$. Found, %: N 15.50. Calculated, %: N 15.84.

EXAMPLE 3

Preparation of
N-methyl-N'-($\beta$-D-xylosyl)-N-nitrosourea

A mixture of 3 g of D-xylose, 1.7 g of methylurea, 0.08 g of nitroaniline, 0.08 ml of a concentrated hydrochloric acid in 12 ml of ethanol is heated at reflux for 10 minutes. The resulting precipitate in the amount of 2.55 g is separated and added with 12 ml of glacial acetic acid, 2.3 ml of distilled water, 1.79 g of sodium nitrite and stirred at the temperature of $-2°$ C. for 2 hours. The residue is filtered-off, recrystallized from an alcohol to give 1.8 g of the product (62% of the theoretical). M.p. 109° C. (decomposition), $[\alpha]_D - 21.9°$ (water), $R_f = 0.66$. Found, %: N 17.62; Calculated, %: N 17.87.

EXAMPLE 4

Preparation of N-ethyl-N'-($\beta$-D-xylosyl)-N-nitrosourea

A mixture of 3 g of D-xylose, 1.9 g of ethylurea, 0.3 g of nitroaniline and 0.2 ml of a concentrated hydrochloric acid is refluxed in 15 ml of ethanol for 10 minutes. The precipitate in the amount of 2.8 g is separated, then added with 15 ml of glacial acetic acid, 2.5 ml of distilled water and 1.74 g of sodium nitrite and stirred for 2 hours at 0° C. The solution is evaporated and recrystallized from an alcohol to give 2.54 g (80% of the theoretical) of the product. M.p. 104° C. (decomposition), $[\alpha]_D - 13.6°$ (water), $R_f = 0.76$. Found, %: N 16,42. Calculated, %: N 16.86.

EXAMPLE 5

Preparation of
N-propyl-N'($\beta$-D-glucosyl)-N-nitrosourea

A mixture of 3.6 g of D-glucose, 2.3 g of propylurea, 0.2 g of nitroaniline and 0.1 ml of a concentrated sulphuric acid is heated at reflux for 10 minutes in 15 ml of methanol. The residue in the amount of 2.6 g is separated, added with 15 ml of glacial acetic acid, 8 ml of distilled water, 1.8 g of sodium nitrite and stirred at the temperature of $-1°$ C. for 2 hours. The solution is evaporated, the residue is recrystallized from methanol to give 2.32 g (80% of the theoretical) of the product. M.p. 110° C. (decomposition), $[\alpha]_D - 5°$ (CH$_3$OH), $R_f = 0.81$. Found, %: N 14.12. Calculated, %: N 14.33.

EXAMPLE 6

Preparation of
N-butyl-N'-($\beta$-D-glucosyl)-N-nitrosourea

A mixture of 3.6 g of D-glucose, 2.8 g of butylurea, 0.2 g of nitroaniline and 0.15 ml of a concentrated hydrochloric acid in 10 ml of methanol is heated at reflux for 20 minutes. The resulting precipitate in the amount of 3 g is separated and added with 15 ml of glacial acetic acid, 10 ml of distilled water, 1.8 g of sodium nitrite and stirred at the temperature of $-1°$ C. for 2 hours to give 2.98 g of the product (90% of the thoretical), hydroscopic, $[\alpha]_D -1°$ (CH$_3$OH), R$_f$=0.85. Found, %: N 13.47. Calculated, % N 13.68.

EXAMPLE 7

Preparation of N-methyl-N'-(α-L-arabinosyl)-N-nitrosourea

A mixture of 3.0 g of L-arabinose, 1.8 g of methylurea, 0.1 g of nitroaniline, 0.1 ml of a concentrated hydrochloric acid in 20 ml of ethanol is heated till dissolution of the precipitate. The formed residue in the amount of 2.5 g is separated and added with 12 ml of glacial acetic acid, 2.5 ml of distilled water, 1.79 g of sodium nitrite and stirred at −2° C. for 2 hours. The solution is evaporated, recrystallized from an alcohol to give 1.99 g (70% of the theoretical) of the product. M.p. 96° C. (decomposition), $[\alpha]_D +6.8°$ (water), R$_f$=0.62. Found, %: N 17.68. Calculated, %: N 17.87.

What is claimed is:

1. A method for preparing an N-alkyl-N'-glycosyl-N-nitrosourea of the formula:

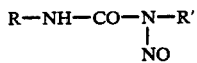 (I)

wherein the nitrosourea is substituted at the first glycoside center and wherein R is glycosyl, R' is a lower alkyl; comprising reacting a non-protected monosaccharide with an alkylurea of the formula:

 (II)

wherein R' is a lower alkyl, in the presence of nitroaniline and a mineral acid in an organic medium, followed by nitrosation of the reaction product.

2. A method as claimed in claim 1, wherein the reaction of said starting components is carried out at the boiling temperature of the mixture thereof.

3. A method according to claim 1, wherein the amount of nitroaniline for the reaction is within the range of from 1.6 to 3.5% by mass.

4. A method as claimed in claim 1, wherein said mineral acid is hydrochloric acid.

5. A method as claimed in claim 1, wherein said mineral acid is hydrochloric acid and said organic medium is methanol.

6. A method as claimed in claim 1, wherein said non-protected monosaccharide is selected from the group consisting of D-glycose, D-galactose, D-xylose, D-glucose, L-arabinose, D-arabinose and D-mannose.

7. A method for preparing an N-alkyl-N'-glycosyl-N-nitrosourea of the formula:

 (I)

wherein R is glycosyl and R' is a lower alkyl; said method comprising reacting in an organic medium a non-protected monosaccharide selected from the group consisting of D-glycose, D-galactose, D-xylose, D-glucose, L-arabinose, D-arabinose and D-mannose, with an alkylurea of the formula:

 (II)

wherein R' is a lower alkyl, in a respective molar ratio of from 1:1 to 1:1.2, and in the presence of nitroaniline and a mineral acid followed by nitrosation of the reaction product with sodium nitrite in the presence of glacial acetic acid and a temperature of from 0° to −2° C.

* * * * *